Figure 1:
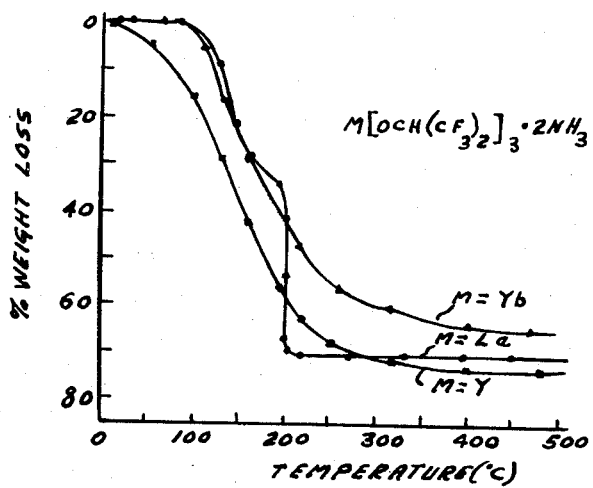

United States Patent [19]
Mazdiyasni et al.

[11] 3,975,416
[45] Aug. 17, 1976

[54] PREPARATION OF YTTRIUM AND LANTHANIDE HEXAFLUOROISOPROPOXIDE DIAMMONIATES

[75] Inventors: Khodabakhsh S. Mazdiyasni, Xenia; Barbara J. Schaper, Enon, both of Ohio

[73] Assignee: The United States of America as represented by the Secretary of the Air Force, Washington, D.C.

[22] Filed: Sept. 6, 1973

[21] Appl. No.: 394,891

[52] U.S. Cl. .............................................. 260/429.2
[51] Int. Cl.$^2$ ........................................... C07F 5/00
[58] Field of Search ................................ 260/429.2

[56] References Cited
OTHER PUBLICATIONS

Kapoor et al., Chemistry & Industry (London), 1968, p. 1314.

Merbach et al., Helv. Chim. Acta. vol. 54., pp. 2771–2772 (1971).

*Primary Examiner*—Leland A. Sebastian
*Attorney, Agent, or Firm*—Joseph E. Rusz; Cedric H. Kuhn

[57] ABSTRACT

Yttrium and rare earth metal hexafluoroisopropoxide diammoniates are prepared by reacting yttrium and rare earth metal chlorides with 1,1,1,3,3,3-hexafluoroisopropanol in the presence of anhydrous ammonia. The compounds are useful as catalysts for organic and polymerization reactions, as dopants for semi-conductor devices, and in preparing thin film coatings.

11 Claims, 2 Drawing Figures

PREPARATION OF YTTRIUM AND LANTHANIDE HEXAFLUOROISOPROPOXIDE DIAMMONIATES

RIGHTS OF THE GOVERNMENT

The invention described herein may be manufactured and used by or for the Government of the United States for all governmental purposes without the payment of any royalty.

FIELD OF THE INVENTION

This invention relates to yttrium and lanthanide hexafluoroisopropoxide diammoniates and a process for their synthesis.

BACKGROUND OF THE INVENTION

The use of anhydrous ammonia in preparing non-fluorinated alkoxides of metals of Group IVb and V, uranium and iron is disclosed in U.S. Pat. No. 2,187,821 (1940) and British Pat. No. 512,452 (1939). More recently, there have been reports in the literature of the use of the ammonia method in the preparation of 2,2,2-trifluoroethoxides of certain Group IV and Group V elements and 1,1,1,-3,3,3-hexafluoroisopropoxides of the same elements. However, attempts to synthesize Group IV metal hexafluoroisopropoxides by the ammonia method produced only poor yields. Furthermore, the products contained metal, fluorinated alkoxides, and in most instances two molecules of ammonia so strongly bonded as to prevent its loss even when heated at relatively high temperatures. Because of the foregoing factors, the products could not be satisfactorily employed as precursors in making high purity metal oxides.

It is an object of this invention to provide a process for preparing in high yield yttrium and lanthanide hexafluoroisopropoxide diammoniates.

Another object of the invention is to provide high purity yttrium and lanthanide hexafluoroisopropoxide diammoniates which upon heating at elevated temperatures decompose to high purity oxides.

Figure 2:
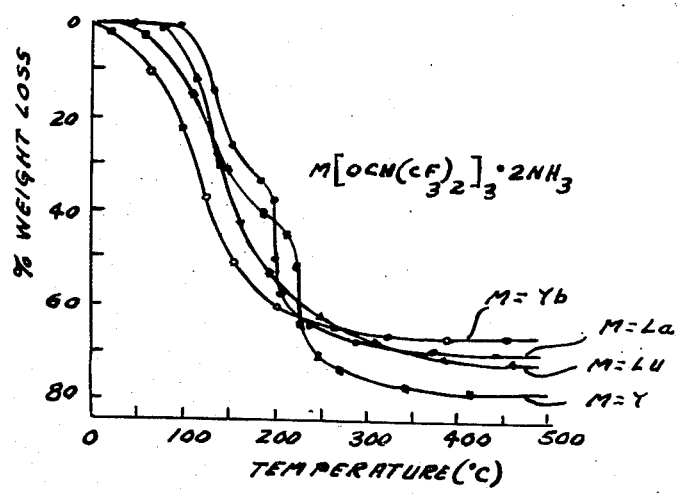

Other objects and advantages of the invention will become apparent to those skilled in the art upon consideration of the following disclosure and the drawing, in which:

FIG. 1 is a graph showing the results of thermal decomposition in a helium atmosphere of certain diammoniates, and FIG. 2 is a graph showing the results of thermal decomposition in ambient air of certain diammoniates.

SUMMARY OF THE INVENTION

Broadly stated, the present invention resides in a process for preparing yttrium and lanthanide hexafluoroisopropoxide diammoniates which comprises reacting a chloride of yttrium or an element of the lanthanide series with 1,1,1,3,3,3-hexafluoroisopropanol (HFiP) in the presence of anhydrous ammonia.

The reaction involved in the process can be represented by the following equation:

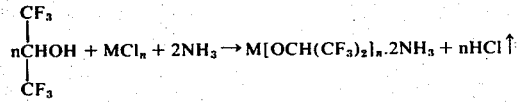

In the equation M is yttrium (Y) or an element of the lanthanide series, i.e., lanthanum (La), cerium (Ce), praseodymium (Pr), neodymium (Nd), samarium (Sm), europium (Eu), gadolinium (Gd), terbium (Tb), dysposium (Dy), holmium (Ho), erbium (Er), thulium (Tu), ytterbium (Yb), and lutetium (Lu). The $n$ in the equation is equal to the valence of the metal M, i.e., 2, 3 or 4.

As shown by the foregoing equation, stoichiometric amounts of the yttrium or rare earth metal chloride are employed in the reaction. Thus, the mol ratio of the chloride to the alcohol is 2, 3 or 4, the valence of the metal M, to 1. In order to obtain maximum yields, it is important to utilize diethyl ether as the solvent or reaction medium. However, the reaction can be conducted in excess alcohol at the expense of obtaining lower yields. The process is conducted under a vacuum or a blanket of an inert gas, such as helium, nitrogen or argon, while introducing anhydrous ammonia into the reaction mixture. It is usually preferred to use an excess of the ammonia, e.g., a molar excess in the range of 20 to 100 percent. The temperature and pressure conditions employed are such as to prevent boiling off the reaction medium. When conducting the reaction in diethyl ether, a temperature in the range of about zero to 5°C and a pressure ranging from about 760 to 780 mm of mercury are used. A temperature below the boiling point of the alcohol, i.e., below about 57°C, is used when the reaction is carried out in excess alcohol.

A period of about 1 to 5 hours is usually sufficient to complete the reaction although longer times can be employed. At the end of the reaction period, the crystalline product obtained is separated from the reaction mixture and then purified. Purification can be accomplished by recrystallization from hot hexafluoro-2-propanol, i.e., by dissolving the crystals in hot alcohol and then cooling, or by vacuum distillation of the reaction mixture at 120° to 140°C and 0.08 mm of mercury.

The diammoniates prepared by the process of this invention possess a high degree of purity. And since the compounds can be thermally decomposed, they can be used as precursors for high purity, submicron size oxide powders. The yttrium and rare earth metal oxide powders so prepared can be employed in manufacturing dense, stable refractory, ferroelectric, piezoelectric, laser, nuclear, phosphor, and electrooptic type materials. The oxide powders are also useful in the stabilization of zirconium oxide, as a sintering aid for densification of silicon nitride, as absorbents and as catalysts.

A more complete understanding of the invention can be obtained by referring to the following illustrative example which is not intended, however, to be unduly limitative of the invention.

EXAMPLE

A series of runs was carried out in which yttrium, lanthanum, praseodymium, samarium, europium, dysposium, holmium, erbium, ytterbium, and lutetium hexafluoroisopropoxide diammoniates were prepared. The yttrium and lanthanide chlorides used were anhydrous and had a purity of 99.9 percent. The 1,1,1,3,3,3-hexafluoro-2-propanol (HFiP), which as obtained had a boiling point of 57°–58°C, was distilled over sodium using a 70 cm Vigreux column. The center fraction (boiling point 57.5°C) was collected and stored in a dark container. The ammonia and diethyl ether were of reagent grade and were dried over Linde activated molecular sieve, Type 4A, before being used.

The runs were carried out in glass apparatus with ground glass joints under reduced pressure or under an atmosphere of dry helium. Compounds were handled in an inert atmosphere and were stored in an evacuated desicattor over phosphorous pentoxide.

Yttrium and lanthanide hexafluoroisopropoxide diammoniates were prepared by reacting the appropriate anhydrous metal halide with HFiP in diethyl ether. During the reaction an excess of anhydrous ammonia was bubbled through the reaction mixture. The mol ratio of metal halide to HFiP was 1:3, except that when using $EuCl_2$ the mol ratio was 1:2. The reactions were conducted at 5°C, and the yields of crude products were from 70 to 80 percent. The crude crystalline products were separated from the reaction mixture and purified by recrystallization from hot HFiP or by vacuum distillation at 120° to 140°C and 0.08 mm Hg. The products were quite soluble in acetone, diethyl ether, and tetrahydrofuran, sparingly soluble in $CFCl_3$, and insoluble in n-hexane and benzene.

The results of the elemental analyses of the products are set forth below in the table. Also listed in the table are the melting points of the compounds.

tion at relatively low temperatures. The thermograms for the ytterbium and lanthanum analogs are significantly different from that for the yttrium compound in the range of 25° to 100°C. There is practically no weight loss from room temperature to 100°C which is an indication of some degree of stability at low temperatures for these compounds. $Yb(HFiP)_3.2NH_3$ loses 58 percent of its total weight gradually with increasing temperature up to 250°C. The thermogram for the La compound is, however, significantly different from those of the Y and Yb compounds. The weight loss for $La(HFiP)_3.2NH_3$ occurs in three consecutive steps at about 150°, 180°, and 190°C, corresponding respectively to 20, 23, and 70 percent of the total weight. Elemental analysis of a separate $La(HFiP)_3.2NH_3$ sample, heated to 180°C for a short time under identical conditions used for the thermogravimetric analysis, indicated zero percent of nitrogen present.

The thermogravimetric analysis results supported by nuclear magnetic resonance data indicate that the mechanism of thermal decomposition for the higher lanthanide hexafluoroisopropoxide ammoniates first involves the gradual and random splitting off of the

TABLE

| Compound[1] | Color | | Carbon % | Hydrogen % | Fluorine % | Metal % | Nitrogen % | mp°C |
|---|---|---|---|---|---|---|---|---|
| $Y(HFIP)_3.2NH_3$ | White | Calcd | 17.32 | 1.45 | 48.71 | 14.25 | 4.49 | 68–70 |
| | | Found | 17.35 | 1.26 | 49.07 | 15.23 | 4.18 | |
| $La(HFIP)_3.2NH_3$ | White | Calcd | 16.03 | 1.34 | 50.71 | 20.60 | 4.15 | 63–65 |
| | | Found | 17.12 | 1.38 | 47.75 | 22.00 | 4.26 | |
| $Pr(HFIP)_3.2NH_3$ | Green | Calcd | 16.00 | 1.34 | 50.61 | 20.85 | 4.15 | 58–60 |
| | | Found | 16.80 | 1.53 | 48.40 | 21.25 | 4.01 | |
| $Sm(HFIP)_3.2NH_3$ | Lt. Yellow | Calcd | 15.78 | 1.32 | 49.86 | 21.88 | 4.08 | 68–70 |
| | | Found | 15.88 | 1.44 | 49.98 | 22.00 | 4.04 | |
| $Eu(HFIP)_3.2NH_3$ | White | Calcd | 13.84 | 1.55 | 43.77 | 29.17 | 5.38 | 65–67 |
| | | Found | 14.35 | 1.43 | 41.26 | 31.00 | 5.06 | |
| $Dy(HFIP)_3.2NH_3$ | Lt. Yellow | Calcd | 15.46 | 1.30 | 48.90 | 23.24 | 4.00 | 61–64 |
| | | Found | 16.00 | 1.27 | 45.88 | 24.26 | 4.4 | |
| $Ho(HFIP)_3.2NH_3$ | Peach | Calcd | 15.44 | 1.29 | 48.83 | 23.55 | 4.0 | 70–73 |
| | | Found | 15.98 | 1.27 | 49.30 | 24.12 | 4.4 | |
| $Er(HFIP)_3.2NH_3$ | Pink | Calcd | 15.35 | 1.29 | 48.56 | 23.75 | 3.98 | 63–64 |
| | | Found | 15.54 | 1.43 | 45.19 | 26.10 | 3.98 | |
| $Yb(HFIP)_3.2NH_3$ | White | Calcd | 15.24 | 1.28 | 48.22 | 24.40 | 3.95 | 72–74 |
| | | Found | 15.67 | 1.44 | 45.24 | 26.24 | 3.67 | |
| $Lu(HFIP)_3.2NH_3$ | White | Calcd | 15.13 | 1.27 | 47.88 | 24.50 | 3.92 | 78–80 |
| | | Found | 15.55 | 1.17 | 45.91 | 26.24 | 3.85 | |

[1]Analysis for chlorine was negative.

Considering the hygroscopic nature of the compounds, the elemental analyses were in good agreement with calculated values. The analyses indicated the absence of chlorine. Both infrared analyses and analyses by nuclear magnetic resonance supported the data obtained in the elemental analyses. In comparison to the non-fluorinated lanthanide alkoxides, the products of this invention, as seen from the foregoing table, have a low melting point in the range of about 60° to 80°C.

Samples of 100 mg were heated in helium or ambient air from room temperature to 1000°C at a rate of 5°C/min. The weight loss was continuously recorded on a Burrell Stanton TR–1 thermobalance. The residue was identified by X-ray powder diffraction analysis.

The results of the thermal decomposition in a helium atmosphere are shown in FIG. 1 of the drawing. As seen from the thermogram for yttrium hexafluoroisopropoxide diammoniate, this compounds loses weight immediately and continuously over the temperature range. The initial 5 percent weight loss from 25° to 60°C is attributed to the loss of some fluorine at a very low temperature. The weight loss from 50° to 250°C, corresponding to about 65 percent of the total weight, is attributed to the loss of $NH_3$ and partial decomposicoordinated ammonia groups in the temperature range of 100° to 150°C and formation of uncomplexed fluoro-substituted isopropoxides which then undergo rapid decomposition to metal fluoroxides. The rate controlling step is the rate of removal of the $NH_3$ groups.

The results of the thermal hydrolysis in ambient air are shown in FIG. 2 of the drawing. As seen from the thermograms, the inflections appear at about the same temperature as in the helium atmosphere but much lower weight loss is observed in the air atmosphere. The thermogram of $Y(HFiP)_3.2NH_3$ in air shows considerable similarity to that of the lanthanide compounds.

The decomposition of known quantities of the Y, Dy and La compounds heated to 600°C for 1 hour resulted in the formation of orthorhombic $YF_3$ and $DyF_3$ and hexagonal $LaF_3$. On increasing the temperature to 800°C, metal oxyfluorides were obtained after 1 hour, and, after heating at 1000°C for longer than 4 hours, the resulting residues were converted quantitatively to the oxides. The oxides were identified by X-ray diffraction. All diffraction lines observed for Y, Dy and La oxides agreed well with the ASTM values for cubic $Y_2O_3$ and $Dy_2O_3$, and hexagonal $La_2O_3$.

As will be evident to those skilled in the art, various modifications of this invention can be made in view of the foregoing disclosure without departing from the spirit or scope of the invention.

We claim:

1. A process for preparing yttrium and lanthanide hexafluoroisopropoxide diammoniates which comprises reacting anhydrous yttrium chloride or an anhydrous lanthanide chloride with 1,1,1,-3,3,3-hexafluoroisopropanol in the presence of anhydrous ammonia, the reaction being conducted at a temperature in the range of zero to 5°C in a reaction medium consisting essentially of diethyl ether.

2. The process according to claim 1 in which the yttrium chloride or lanthanide chloride is reacted with 1,1,1,3,3,3-hexafluoroisopropanol in stoichiometric amounts using a molar excess of anhydrous ammonia.

3. The process according to claim 2 in which a molar excess of anhydrous ammonia in the range of 20 to 100 percent is used.

4. The process according to claim 2 in which the diammoniate is separated from the resulting reaction mixture; the separated diammoniate is dissolved in 1,1,1,3,3,3-hexafluoroisopropanol; and the solution obtained is cooled, thereby causing the diammoniate to recrystallize as a purified product.

5. The process according to claim 2 in which the lanthanide chloride is a chloride of lanthanum, cerium, praseodymium, neodymium, samarium, europium, gadolinium, terbium, dysposium, holmium, erbium, thulium, ytterbium or lutetium.

6. As a new composition of matter, a compound having the following formula:

$$M[OCH(CF_3)_2]_n \cdot 2NH_3,$$

wherein M is an element selected from the group consisting of yttrium, lanthanum, cerium, praseodymium, neodymium, samarium, europium, gadolinium, terbium, dysposium, holmium, erbium, thulium, ytterbium, and lutetium, and $n$ is a numeral equal to the valence of the element M.

7. The composition of claim 6 in which M is yttrium and $n$ is equal to 3.

8. The composition of claim 6 in which M is lanthanum and $n$ is equal to 3.

9. The composition of claim 6 in which M is ytterbium and $n$ is equal to 3.

10. The composition of claim 6 in which M is lutetium and $n$ is equal to 3.

11. The composition of claim 6 in which M is praseodymium and $n$ is equal to 3.

* * * * *